(12) United States Patent
Livaditis (10) Patent No.: US 6,382,968 B2
(45) Date of Patent: May 7, 2002

(54) ELECTROSURGICAL TOOL FOR TISSUE COAGULATION IN VITAL PULP THERAPY

(76) Inventor: Gus J. Livaditis, 2328 Marlboro Dr., York, PA (US) 17403

( * ) Notice: Subject to any disclaimer, the term of this patent is extended or adjusted under 35 U.S.C. 154(b) by 0 days.

(21) Appl. No.: 09/862,544

(22) Filed: May 22, 2001

Related U.S. Application Data (63) Continuation-in-part of application No. 09/624,116, filed on Jul. 24, 2000.

(51) Int. Cl.$^7$ ................................................ A61C 3/00
(52) U.S. Cl. ........................................... 433/32; 606/50
(58) Field of Search ................................ 433/224, 215, 433/32; 606/48, 49, 50

(56) References Cited

U.S. PATENT DOCUMENTS

| | | | |
|---|---|---|---|
| 4,674,499 A | | 6/1987 | Pao ..................... 128/303.14 |
| 4,766,896 A | | 8/1988 | Pao ........................... 128/305 |
| 4,805,616 A | | 2/1989 | Pao ...................... 128/303.17 |
| 4,885,004 A | | 12/1989 | Pao ............................. 604/22 |
| 5,192,280 A | * | 3/1993 | Parins ......................... 606/48 |
| 5,421,727 A | | 6/1995 | Stevens et al. ............. 433/224 |
| 5,484,435 A | * | 1/1996 | Fleenor et al. ............... 606/46 |
| 6,015,406 A | * | 1/2000 | Goble et al. .................. 606/41 |
| 6,238,394 B1 | * | 5/2001 | Garito et al. ................. 606/41 |

OTHER PUBLICATIONS

"Intentional Pulp Capping: A Clinical Perspective of the Adhesive Experience", Liebenberg, W.H., *J. Adhes. Dent.*, vol. 1, No. 4, pp. 345–363 (1999).
"The Principles of Surgical Diathermy and Its Limitations", Mitchell et al, *Brit. J. of Surgery*, 50, pp. 314–320 (1962).
"The Effect of Electrosurgery on Alveolar Bone", Azzi et al, *J. Periodontol.*, vol. 54, No. 2, pp. 96–100 (1983).
"Effects of Electrosurgery on Dog Pulps Under Cervical Metallic Restorations", Krejci et al, *Oral Surg.*, vol. 54, No. 6, pp. 575–582 (1982).
"Pulpal Effects of Electrosurgery Involving Based and Unbased Cervical Amalgam Restorations", Spangberg et al, *Oral Surg.*, vol. 54, No. 6, pp. 678–685 (1982).
"Pulpal and Periodontal Effects of Electrosurgery Involving Cervical Metallic Restorations", Robertson et al, *Oral Surg.*, vol. 46, No. 5, pp. 702–710 (1978).
"Pulpotomy by Electro–Coagulation", Laws, A.J., *The New Zealand Dental Journal*, vol. 53, pp. 68–70 (1957).
"Bipolar Electrode for Electrocoagulation of the Inferior Turbinate", Herd, L.M., *Archives of Otolaryngology*, p. 442 (1931).
"Two Point Coagulation", Greenwood, Jr., J., *Am. J. Surg.*, New Series vol. L, No. 2, pp. 267–270 (1940).
"Coaxial Bipolar Probe", Pao, D.S.C., *Arch. Ophthalmol.*, vol. 97, pp. 1351–1352 (1979).
"A Bipolar Coaxial Microprobe for Safe Transvitreal Diathermy", Parel et al, *Arch. Ophthalmol.*, vol. 99, pp. 494–497 (1981).
Elmed Company Brochure entitled "Radiofrequency Energy Proves to be Effective Against a Major Cause of Obstructive Sleep Apnea", 2 pages (1998).
Elmed Company Brochure entitled "The Surgical Treatment of Snoring", 2 pages (1998).

* cited by examiner

*Primary Examiner*—John J. Wilson
*Assistant Examiner*—Melba Bumgarner
(74) *Attorney, Agent, or Firm*—Synnestvedt & Lechner LLP (57) ABSTRACT

An electrosurgical tool for coagulating a tissue layer is disclosed, having a hand piece with an electrical coupling at one end and a head mounting a bipolar coaxial electrode at the other end. The electrode is rotatable about its long axis and has an end face where the two poles of the electrode are exposed. The end face is asymmetrically arranged with respect to the long axis and allows the same tool to be used to coagulate exposed pulp on opposite tooth faces by manually rotating the electrode. An electrosurgical unit connected to the electrical coupling powers the tool. Electrodes are interchangeable and may be straight or curved and have a dome-shaped or cut-back end face.

25 Claims, 7 Drawing Sheets

ELECTROSURGICAL TOOL FOR TISSUE COAGULATION IN VITAL PULP THERAPY

RELATED APPLICATION

This is a continuation-in-part of U.S. application Ser. No. 09/624,116, filed Jul. 24, 2000.

FIELD OF THE INVENTION

The present invention is directed to an apparatus for providing hemostasis of dental pulp. In particular, the present invention is directed to an electrosurgical coagulation tool which provides durable hemostasis to exposed dental pulp with little or no damage to the pulp.

A. The Anatomy of the Tooth

Teeth, both primary and permanent, consist of outer enamel, an inner layer of dentin, and a soft tissue component referred to as the dental pulp. The pulp is enclosed by dentin, is continuous with soft tissue in the tooth socket, begins at the tip of the root, traverses through each root and terminates in the pulp chamber of the coronal or visible portion of the tooth. Initially, the dental pulp is responsible for the development of the enamel and dentin and later continues to provide the blood supply, nerve enervation and lymphatic drainage. The pulp responds to insult by depositing reparative and secondary dentin to protect the pulp and initiates an inflammatory process to combat bacterial infection.

B. Injury to the Pulp

The tooth and pulp are typically threatened in a variety of ways: (1) fracture of the tooth exposing the pulp to bacteria normally present in the oral cavity; (2) dental caries (decay) which decalcifies enamel and dentin, exposes the pulp and allows ingress of bacteria and bacterial products, (3) dental restorative procedures which may inadvertently expose the pulp; and (4) failure of dental restorations through fracture or leakage, including microleakage, allowing bacteria or bacterial by-products to reach the pulp. For decades many factors have been blamed for causing inflammation and necrosis (i.e., non-vitality, death) of the dental pulp, including: (1) dental caries and associated bacteria being the most prominent; (2) fracture and exposure to bacteria; (3) excess heat from dental instrumentation; and (4) toxicity of dental materials. More recently, bacterial invasion via microleakage has been attributed as an important cause of pulpal inflammation and necrosis.

Traditionally, when a small exposure of the pulp occurred mechanically, by fracture of the tooth, or while excavating caries, the exposure was promptly 'capped' with various dental materials in an attempt to prevent inflammation or necrosis of the pulp. If the exposure was small and capping occurred immediately and with a suitable material, pulpal necrosis could be averted. However, if the exposure was moderate or large in size, or if capping occurred after bacteria developed a foothold, or if the capping material deteriorated leading to microleakage, then inflammation or necrosis would typically occur. Materials (e.g., calcium hydroxide) which stimulated reparative dentin formation were used for capping of the pulp for over half a century in an attempt to stimulate health and to restore the pulpal wall naturally via slow deposition of reparative dentin.

C. Treatment Methods for Exposed Pulp

If the pulp progressed to necrosis, only two options were available to the patient: (1) extraction of the tooth; or (2) extirpation of the necrotic pulp and filling of the pulpal space with a suitable material to prevent microleakage via the pulp space to the surrounding bone. This second alternative is referred to as endodontic therapy (root canal treatment). Inflamed vital dental pulps, however, represent a substantial portion of infected pulps. Additionally, pulps exposed intentionally for therapeutic purposes (e.g., to support a denture) also constitute a significant portion. These latter two groups are currently relegated to extraction or endodontic therapy despite their vitality. Inflamed but vital pulps are considered, under current clinical guidelines, to be untreatable. Even teeth with relatively mild symptoms are diagnosed as "irreversible pulpitis" and condemned to extraction or endodontic therapy.

Over the past seven decades, the research primarily centered around the stimulation of reparative dentin deposition and pulp therapy was limited to small exposures on asymptomatic teeth. A few reported exceptions involved more aggressive pulp therapy but was limited to adolescent and young adult patients. Several developments in the field opened the possibility of more comprehensive pulp therapy. These included: (1) The realization that most pulpal inflammation is due to bacteria invasion and bacterial by-products occurring via microleakage and less due to toxicity of dental materials; and (2) The development of materials that adhere to dentin and which can produce a seal to prevent microleakage (i.e., dentin adhesion products and the ability to create a hybrid layer consisting of collagen and resin). The ability to stimulate the deposition of reparative dentin became a standard for demonstrating re-organization and healing of the pulp after an insult. Despite these developments, only teeth with small exposures or mild clinical symptoms were routinely treated while the great majority of teeth exhibiting pulpal inflammation or periapical inflammation (inflammation of a pulpal origin in the bone around the tip of the root) were treated with endodontic therapy or extraction of the tooth.

One of the obstacles in treating the pulp is the impact of bleeding on the formation of the pulp barrier (sealing of the pulp or the restoration of the missing pulpal wall). Bleeding during any surgical procedure can impact on the success of treatment ranging from (1) being a mere nuisance or compromising visibility to (2) creating a toxic reaction (as in neurosurgery). Bleeding around the retina during eye surgery, for example, is an important concern. In pulp therapy, bleeding compromises visibility, jeopardizes the dentin adhesion and creates voids or tracts within the barrier material resulting in chronic irritation and failure of the pulp therapy. In a very common situation, pulp therapy cannot be instituted because the hemorrhaging cannot be controlled. In these cases, the teeth are relegated to endodontic therapy or extraction simply due to the uncontrolled bleeding. One might wonder why bleeding cannot be controlled in an exposure approximately 2–4 square mm in area and consisting of very small blood vessels when bleeding is routinely controlled in major surgical procedures where much larger vessels are involved. A good analogy can be made with ophthalmic surgery where even minor amounts of bleeding during the procedure can compromise the overall therapeutic effort. In pulp therapy, minor bleeding contaminates the surface of the dentin preventing adhesion of the pulp barrier and jeopardizing the valuable dentinal seal. Residual blood clots have been reported to prevent healing and even stimulate an inflammatory response by the release of chemotactic components.

Another important dilemma is that the bleeding must be controlled with little or no injury to the remaining pulp tissue. Furthermore, hemostatic procedures and materials which do not impact on the highly technique-sensitive dentinal adhesion process must be selected. These two factors place severe restrictions on the ability to control bleeding. Furthermore, temporary hemostasis is not sufficient since numerous procedures are required to create the pulp barrier and final restoration—any of which can cause recurring bleeding at a critical moment. Therefore, durable hemostasis is required with minimal or no injury (especially lasting injury) to the pulp. The present invention provides an apparatus which satisfies the need in the art for durable hemostasis.

Reported Developments

Most efforts in controlling bleeding of the pulp involved application of a cotton pellet and light pressure until hemorrhaging ceased. This proved fairly effective with very small exposures but was ineffective with larger exposures or hyperemic pulps. Over the past century, pulpotomy procedures were quite common upon exposure of the pulp. Pulpotomy procedures typically remove the chamber portion of the pulp (the part of the pulp enclosed by the clinical crown, the visible portion of the tooth, as opposed to the pulp tissue contained within the root portion). This allowed control of bleeding at the more constricted portion of the pulp which was easier to accomplish. However, it meant sacrificing a substantial segment of vital pulp tissue. This approach is still quite common in children's primary teeth.

Numerous vasoconstricting (blood vessel contracting) medicaments and even necrotizing materials have been used partly for hemorrhage control and partly for therapeutic purposes. More recently, with greater attention to gentle treatment of the pulp, the selection of materials or medicaments were directed at hemorrhage control with minimal effect on the pulp tissue and with minimal impact on the dentin adhesion procedures. Sodium hypochlorite (2–5%) has been advocated for use in this manner. The present state of the art in pulpal hemostasis consists of: (1) cotton pellet—dry, moist with water, or moist with saline; (2) Sodium hypochlorite (2–5%) applied and rinsed; or (3) failing to achieve hemostasis—referral for endodontics or extraction.

Monopolar electrosurgery uses an active electrode which is very small in dimension compared to the grounding electrode (referred to as the dispersive electrode). The applied power concentrates the current at the narrow point or blade of the active electrode. When sufficiently high, the current is released to the less conductive tissue via direct contact or as a spark that jumps to the tissue. The intense heat that is generated by this sequence of events, which occurs thousands of times per second, coagulates the tissue next to the active electrode. With the monopolar mode, the current then dissipates through the body of the patient via a path of least resistance to the dispersive electrode. Serious consequences have been reported associated to this dispersive path. In particular, there is the potential for necrosis of the pulp, never before realized in dentistry and identified by the inventor, due to a channeling effect of the dissipating current passing through a constriction of the tissue. Monopolar electrosurgery has been used in pulp therapy to fulgurate the pulp. Fulguration is the destruction or ablation of tissue caused by delivering a high frequency electrosurgical current. An electrode is applied a short distance from the tissue and a series of high intensity sparks are caused to jump from the electrode to the tissue causing ablation of the tissue. Fulguration was used much like formocresol, silver nitrate and other materials to coagulate, necrotize, cauterize, etc., a layer of tissue or the entire pulp. Fulguration also provided hemostasis although it is not clear whether it was ever used solely for hemostasis. Fulguration was shown to adversely affect the pulp and tissue surrounding the tooth. The hazards of using monopolar electrosurgery on the dental pulp or near metallic restorations in the tooth, has been reported in a number of publications. These hazards are related to the monopolar mode of electrosurgery, and accordingly, monopolar electrosurgery is contraindicated for use on or near the dental pulp.

SUMMARY OF THE INVENTION

The apparatus concerns an electrosurgical tool for use with a bipolar electrosurgical power unit for coagulating a tissue layer, for example, exposed pulp of a tooth. The tool has an elongated hand piece with a butt end and a head oppositely disposed. An electrical coupling is mounted on the butt end and adapted to connect electrically to the electrosurgical power unit. An electrically conductive pathway is arranged lengthwise along the hand piece and is connected to the electrical coupling. An elongated electrode is mounted on the head and connected to the electrically conductive pathway, the electrode being rotatable about its long axis and oriented at an angle relatively to the hand piece.

Preferably, the electrode is a coaxial bipolar electrode having a first electrode pole coaxially surrounded by a second electrode pole, an insulating layer being coaxially positioned between the first and the second poles. The electrode has an end face positioned distally to the head and asymmetrically arranged with respect to the long axis of the electrode. In one embodiment, the end face is formed by extending the first electrode pole lengthwise beyond the second electrode pole, the end face being oriented at an angle, asymmetrically relatively to the long axis by curving the electrode. In another embodiment, the end face is a cut-back region at the tip of the electrode formed by removing a lengthwise portion of the second pole and the insulating layer along one side of the electrode to expose the first pole along a portion of the one side.

Preferably, the head has a socket sized to receive the electrode for mounting it on the head, the socket having electrical contacts positioned therein, connecting the electrode to the electrically conductive pathway. The socket has a diameter smaller than the electrode to provide an interference fit to frictionally retain the electrode and allow it to rotate about its long axis but also retain its set position against light contact of the end face with a surface.

DETAILED DESCRIPTION OF THE INVENTION

A. Introduction

The methods and apparatus of the present invention relate to bipolar electrocoagulation to preserve and restore the health of the dental pulp. While procedures for preserving the health of the dental pulp are currently available, the present invention expands this capability to teeth with larger pulp exposures which were heretofore not amenable to pulp therapy. Despite the teaching in the prior art, the apparatus of the present invention is not limited by the size of the pulp exposure.

The mildest form of pulpal involvement are those teeth with pulps which are exposed and which do not include any significant pre-treatment pulpal pathology. The pulps of these teeth are typically exposed (1) inadvertently while restoring the tooth for objectives unrelated to the pulp; (2) intentionally exposed to allow alignment of the tooth with other teeth during crown and fixed bridge procedures; and (3) intentionally exposed when the teeth are trimmed to the level of the gum and used for support of an overdenture. Teeth which have been inadvertently exposed have been treated frequently and successfully using calcium hydroxide and more recently resin "capping materials" when the pulp exposure was small. With moderate or large exposures, pulp capping was not applied routinely or effectively.

Pulps exposed during tooth reduction for crowns (caps) or fixed bridges were pulp capped less frequently and were usually directed to endodontic procedures. This was because pulp capping has not been considered a predictably successful procedure even with asymptomatic pulps and small exposures. In contrast, endodontic therapy is viewed as a predictable mode of treatment (90+ percent success). Rather than risk having to perforate the permanent crown for access in accomplishing endodontic therapy after the crown has been cemented, teeth were often referred for endodontic therapy upon exposure of the pulp and prior to fabricating the permanent crown. Another disadvantage with crown procedures is that tooth reduction at the pulp exposure site did not provide space for capping materials and such materials often dislodged. The present invention overcomes this problem by specifically designing the exposure site for the pulp barrier material, i.e., the pulpal wall is prepared with retention form, resistance form, and space for the resinous barrier material in the actual restoration of the wall.

The present invention also provides for teeth (intentionally) exposed for use under overdentures. Teeth are trimmed to the level of the gum typically exposing the pulp. Such teeth have routinely been treated with endodontic therapy. No successful efforts at maintaining the integrity of the pulpal tissue in the root portion can be found in the literature. The present invention preserves the integrity of the remaining pulp tissue by a specific preparation of the exposure site and restoration of the opening with a resinous barrier. The present invention accordingly allows teeth to be saved and improves the stability and function of traditional complete dentures.

Teeth exhibiting pulpal inflammation (pulpitis) and without accompanying periapical lesions are considered to include greater pathology than the intentional or mechanically exposed pulps since these pulps have been exposed to bacteria contained in the carious lesion or directly to the oral cavity. These teeth are routinely diagnosed as "irreversible pulpitis" and relegated to endodontic therapy or extraction. When acute pain is associated with other clinical tests, the decision to treat endodontically is more universal by current criteria. The present invention treats the dental pulp as opposed to removing the pulp or tooth in all degrees of pulpitis. These diseased teeth may range from nuisance level of discomfort to the acutely painful tooth typically referred to as a toothache or abscessed tooth.

Teeth exhibiting a periapical lesion (apical periodontitis) are considered the most severe form of pulpal inflammation just short of necrosis. (A periapical lesion is inflammation extending beyond the pulp to the tissue and bone around the apex of the root, hence the term "periapical". Such lesions are characterized by a breakdown of the bone resulting in a radiolucency on X-rays.) Many dentists assume that the pulp is necrotic when such a lesion is seen on a dental radiograph. The presence of a periapical lesion is almost universally accepted as an irreversible pulpitis or necrosis of the pulp. Indeed, while terms such as "degenerating" or "degenerated" periapical lesion delineating the various states of pulpal pathology are described in dental texts, no comparable terms such as "regenerating" periapical lesions are included in the classification systems. This clearly signifies that the potential for pulpal healing or treatment is not currently acknowledged by the dental profession.

While a necrotic pulp may be irreversible, pulpal and periapical inflammation may be successfully treated using the apparatus and methods of the present invention. In particular, the methods and apparatus of the present invention facilitate reversal of periapical lesions.

B. Hemostasis

Before describing specific features and applications of bipolar electrocoagulation in pulp therapy and restorative dentistry, the importance of the present invention to hemostasis should be understood.

Hemostasis is described in the medical literature to occur in one of two ways: (1) Coaptive—whereby the vessel is grasped and clipped, ligated, coagulated (electrosurgically welded), or otherwise closed by bringing the walls of the vessels together. This form is typically used with larger vessels and may also involve coagulation of the vessel contents and shrinkage of the vessel walls; (2) Obliterative—whereby the vessels and contents are chemically treated or coagulated (by electrosurery or laser) so that the resulting shrinkage of the vessel walls and blockage of the vessel lumen by the coagulated vessel contents enables control of bleeding. This form is typically used with small blood vessels where grasping of the vessel would be difficult or impossible. Only the obliterative form of hemostasis is applicable to pulp therapy. Vessels are typically very small and access to vessels is impossible as they are encased in a small chamber with hard tissue walls (dentin).

While lasers can create precise coagulation of the surface tissue, precision is essentially compromised by the presence of blood on the surface of the pulp or other tissue. With a laser, and previous monopolar or bipolar electrocoagulation methods, blood is coagulated as well as the tissue. The impact of the electrical current or laser beam is affected by the coagulating blood, thus, compromising the precision of coagulation even though some coagulation will occur. The present invention supersedes laser applications in pulp therapy. For example, a coaxial electrode can be positioned in direct contact with the exposed pulp tissue despite a pool of blood and the surface of the tissue can be precisely coagulated.

The precise coagulation of the present invention allows the creation of a layer of desiccation. The term "desiccation" refers to a specific level of coagulation between white coagulation, which is coagulation at a lower temperature and black coagulation, which is coagulation at a higher temperature often resulting in charring of the tissue. Desiccation has been described in the medical literature as the optimum level of coagulation for hemostasis.

C. Bipolar Electrocoagulation

There are two types of electrosurgery, monopolar and bipolar electrosurgery. Electrosurgery has been in use in medicine and dentistry for almost a century. In dentistry, it has been limited exclusively to the monopolar variety except for limited use of bipolar electrosurgery by oral surgeons. Both monopolar and bipolar modes use an alternating electric current with a sinusoidal waveform in the frequency range 500 KHZ to 4.0 MHZ. The monopolar mode was the first to be developed (over a century ago) while the bipolar mode was introduced by L. M. Hurd (Bipolar Electrode for Electrocoagulation of the Interior Turbinate, *Arch. of Otolaryngol,* 1931; 13:442) and later introduced to neurosurgery in the 1940's (Greenwood, J., *Arch. Phys. Ther.,* 23:552–554 (1942)). Both modes can generate coagulation of tissue while the monopolar mode is superior in cutting capability. The high frequency current possesses both traditional electric current properties and radiating properties. The significant difference between the two modes is the path of the dissipating current.

In the bipolar mode, the dissipating current flows directly to the dispersive electrode which is typically the same size and very close to the active electrode (Greenwood, supra refers to it as "two point coagulation"). The only tissue involved in the dissipating current is the tissue between the two electrodes. Thus, bipolar electrosurgery provides substantially greater safety by avoiding involvement of major vessels, nerves or other critical tissues or organs. The bipolar mode requires approximately 20% of the current to create the same degree of coagulation—an additional safety feature by reducing the potential for capacitive coupling.

The present invention applies a combination of either a dual-prong or preferably a coaxial electrode with a bipolar microsurgical unit to generate precise coagulation on the dental pulp without deep injury to the pulp. The present invention represents the first application of bipolar electrosurgery of any form for hemostasis in pulp therapy. The combination of bipolar electrodes, bipolar microsurgical unit, and electronic timer generates an even higher level of precision and safety when coagulating the surface of the dental pulp.

D. Electrodes

Bipolar electrodes can be categorized in one of three groups: (1) Bipolar forceps with each forceps tip individually wired are used to grasp tissue or vessels for coagulation; (2) Two-prong electrodes with a fixed distance between the electrodes which allows coagulation of the tissue between the two points. Two point electrodes have been adapted in the present invention to enable coagulation of pulpal and gingival tissue; and (3) Coaxial electrodes utilized in ophthalmic surgery which consist of an outer tube and an inner insulated wire forming respective outer and inner electrode poles. Coagulation occurs in a circular "footprint" approximately the size of the end of the coaxial electrode. The present invention has adapted and refined the use of the coaxial electrode for use in pulp therapy.

For purposes of bipolar coagulation, blood is a conductive tissue and substantially influences the degree of coagulation, zone of coagulation, optimal power output and the path of the current. Indeed, blood behaves much like tissue and in some aspects is more susceptible to coagulation. For example, relatively dry tissue is less susceptible to coagulation than moist tissue. This is probably due to the conductivity at the interface of electrode and tissue. Blood enhances the conductivity at the interface. Unfortunately, it also allows dissipation of the electrosurgical current creating a wider and unpredictable zone of coagulation. These variations apply to monopolar electrosurgery and to most forms of bipolar electrosurgery. An important exception is the bipolar coaxial electrode. Blood in the field influences the behavior of the coaxial electrode minimally provided the electrode is placed in contact with the surface of the tissue and not just in contact with blood. Typical bipolar electrodes, on the other hand, will coagulate both the blood and tissue affecting the power delivered to the tissue. The exposed prongs of the other electrodes allow dissipation of current around the electrode creating a more diffuse coagulation. The highly desirable precision in coagulation is lost.

The selection of a coaxial bipolar electrode [as opposed to a parallel fixed-position dual-prong electrode (FPDP) or a variable-position dual-prong electrode (VPDP, forceps-type)] is a crucial factor in establishing a high level of consistency in treatment of dental pulps. In pulp therapy, a very shallow zone of coagulation is critical to the success of pulp therapy. The coaxial electrode is self-limiting in area and depth of coagulation and the area of coagulation is more consistent (a circular zone of coagulation determined by the "footprint" of the electrode) than other types of electrodes. Furthermore, the total zone of coagulation is much more consistent than with other types of electrodes. The current at the inner electrode pole is limited in flow to the encircling outer electrode pole confining the coagulation to the diameter of the outer tube. As the current coagulates the tissue between the inner and outer electrode poles, the resulting increased resistance (impedance) of the tissue prevents further or deeper coagulation.

Coagulation in the bipolar mode always requires contact of the electrode with the tissue. However, with the FPDP and VPDP electrodes if the electrode penetrates the tissue surface, additional coagulation will occur throughout the length of the immersed segments of the electrode. Indeed, the depth of penetration will proportionately determine the depth of coagulation. This is undesirable in pulp therapy. The coaxial electrode behaves differently. Since the inner electrode pole is encased within the outer electrode pole, and since there is no tissue between the inner and outer electrode poles except where the inner electrode pole exits the outer electrode pole, coagulation is limited to the end-surface of the electrode. Furthermore, as soon as the tissue at the tip of the electrode becomes coagulated, the impedance increases preventing further flow of current (within reasonable power levels). Therefore, the zone of coagulation varies little whether the coaxial electrode touches only the surface or penetrates the surface. Under both conditions, the resulting coagulation takes the form of a thin disc with the diameter of the electrode. Coagulation along the shaft of the coaxial electrode does not occur.

E. Detailed Description of the Apparatus

Figures 1, 2:
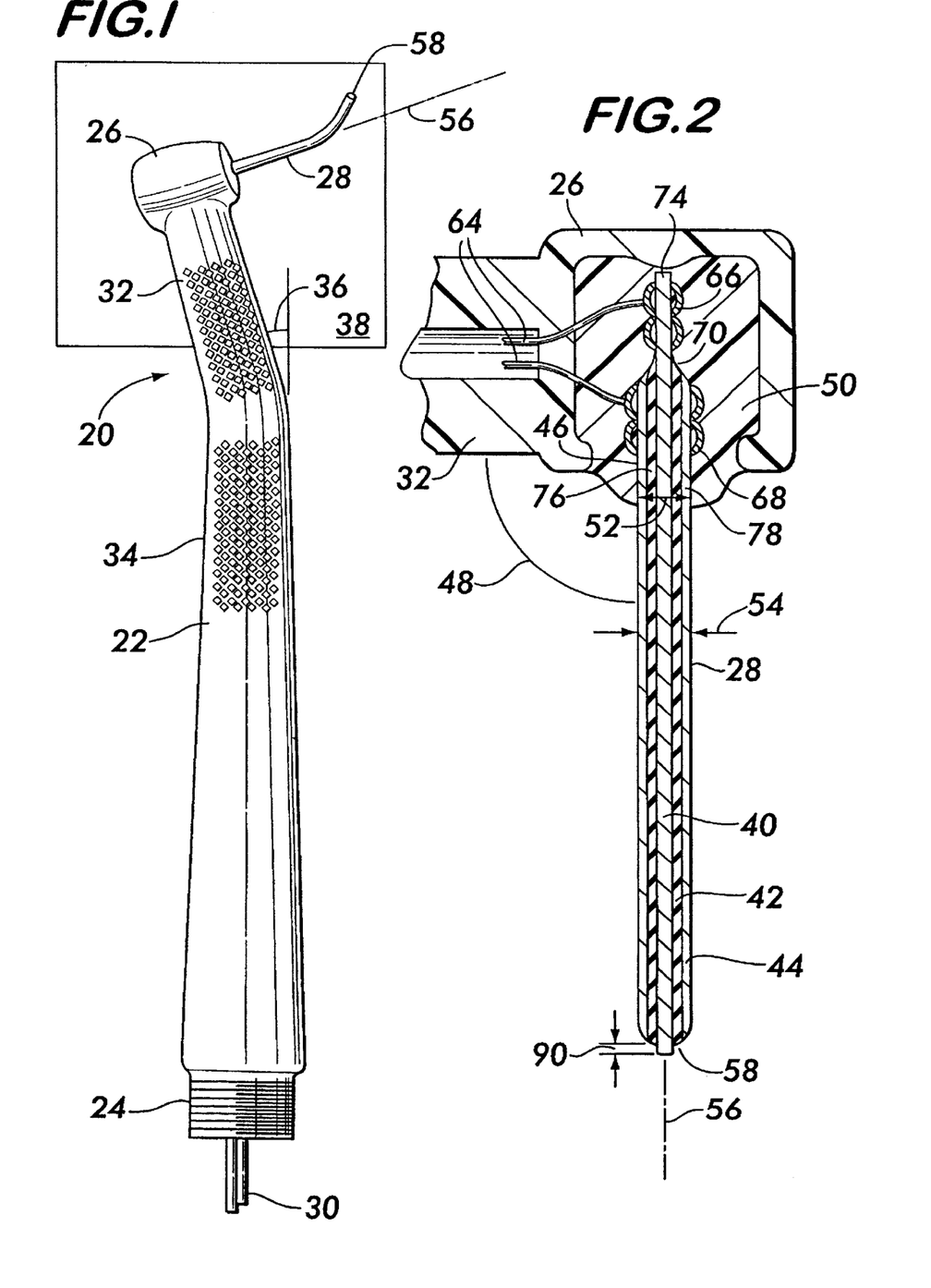
FIG. 1 is a side view of an electrosurgical tool according to the invention.
FIG. 2 is a detailed sectional view of a portion of the tool.

FIG. 1 shows the electrosurgical tool 20 according to the invention. Tool 20 has an elongated hand piece 22 with a butt end 24 and a head 26 positioned opposite the butt end. An elongated electrode 28, described in detail below, is mounted on and extends outwardly from the head. An electrical coupling, preferably in the form of standard male prongs 30 for electrically coupling to a power cord of an electrosurgical unit (not shown, described below) is mounted on the butt end.

Hand piece 22 is formed of a neck portion 32 adjacent to the head 26 and a grip portion 34 positioned between the neck portion 32 and the butt end 24. Neck portion 32 is preferably oriented at an angle 36 relatively to the grip portion 34. Angle 36 is preferably between about 20° and 30° and most preferably at about 25° to accommodate the curves of the dental arches and allow improved access of the electrode 28 to various tooth surfaces within the oral cavity. The angular orientation of neck portion 32 also enables a relatively wide range of angular movement of the hand piece within the oral cavity about the head 26 within a plane 38 defined by the neck portion 32 and the electrode 28.

Hand piece 22 is preferably made from durable, lightweight, inexpensive material, for example, plastic such as polytetrafluoroethylene. Hand pieces made of these materials are less likely to damage tooth surfaces should they come in contact with them, will withstand repeated sterilization providing a relatively long useful life and yet be easily and economically replaceable when they wear out. Use of lightweight material allows the tool to be maneuvered easily within the confines of the oral cavity and reduces user fatigue, allowing for precise, steady positioning of the electrode at a desired position. As a practical matter for ease of handling and use, the grip portion 34 is preferably about 10 cm in length and 6 to 10 mm in diameter. The neck portion is preferably between about 2 and 3.5 cm in length and about 5–6 mm in diameter.

FIG. 2 shows a detailed cross-sectional view of head 26 and electrode 28. Preferably, electrode 28 is a coaxial bipolar electrode having an inner electrode pole 40 positioned within an insulative sleeve 42 and an outer electrode pole 44 in the form of a tube surrounding the sleeve 42 coaxial with the inner pole 40. Electrode 28 fits within a socket 46 within the head 26 and is preferably oriented at an angle 48 with respect to the hand piece. Angle 48 is preferably about 90° relative to the neck portion 32, but may be between 0° (parallel to the neck portion) to about 135° for practical applications.

Figures 3, 6, 7, 8, 9:
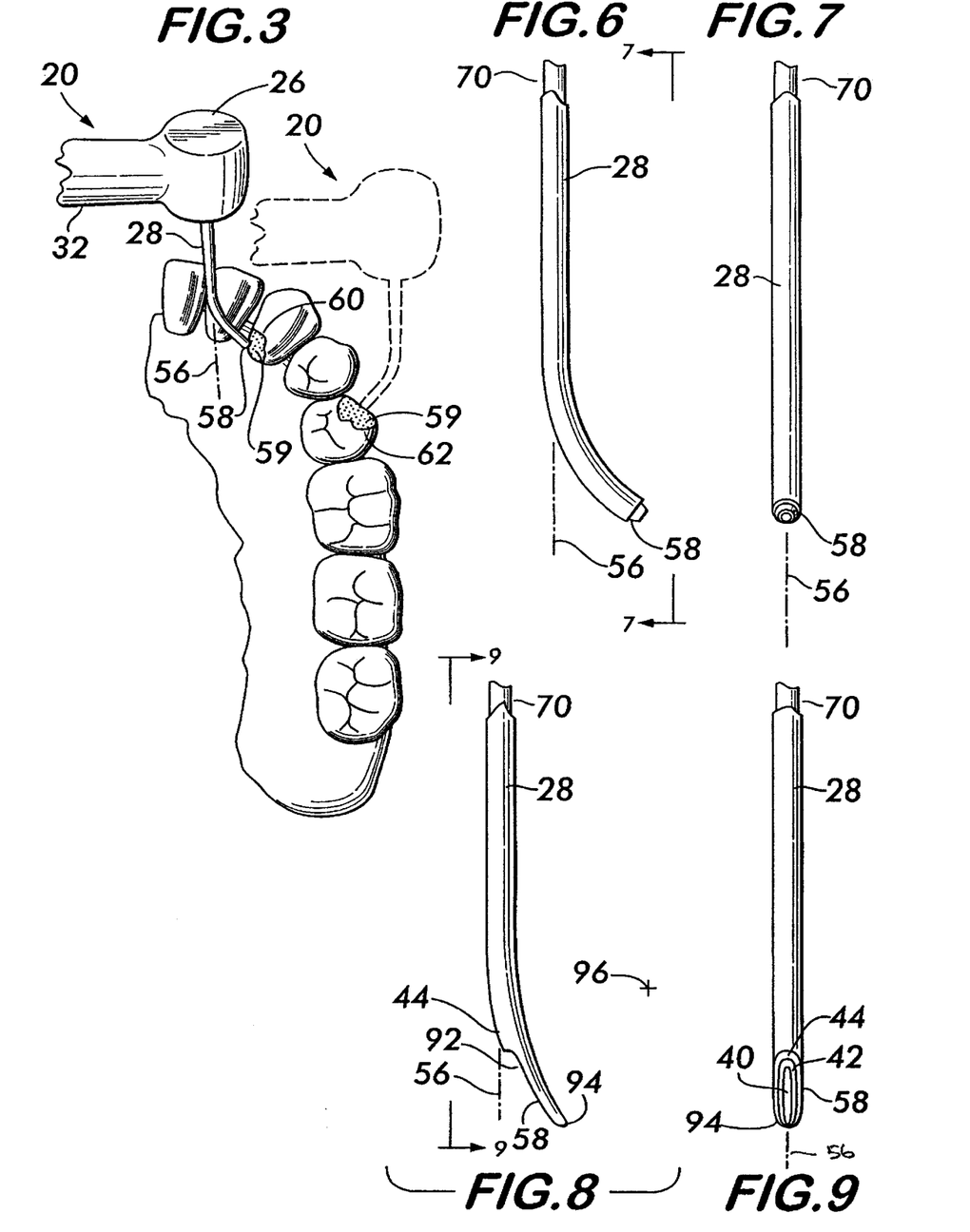
FIG. 3 is a perspective view of the tool in use.
FIG. 6 is a side view of a component of the tool.
FIG. 7 is a view of the component shown in FIG. 6 taken along lines 7—7.
FIG. 8 is a side view of a component of the tool.
FIG. 9 is a view of the component shown in FIG. 8 taken along lines 9—9.

Socket 46 is preferably formed within a body 50 of flexible, resilient, insulating material such as plastic and has a diameter 52 sized slightly smaller than the outer diameter 54 of the electrode to receive the electrode in an interference fit. The interference fit develops friction between the body 50 and the electrode 28, thereby retaining the electrode within the socket but allowing it to be easily removed to interchange or replace electrodes. The interference fit also allows the electrode to be rotated about its long axis 56 relatively to hand piece 22. Allowing the electrode 28 to rotate about its long axis 56 provides a significant advantage for electrodes having an end face 58 which is asymmetrically positioned relatively to the long axis (either because the electrode is curved as shown in FIG. 1, or the end face is cut back as described below). The advantage is illustrated in FIG. 3 wherein the same tool 20, shown in solid and dashed line, may be used to coagulate exposed pulp 59 on opposite tooth surfaces 60 and 62 because the end face 58 is asymmetrically positioned with respect to the long axis 56 (in this example, by curving the electrode). The operator need only withdraw the tool from the oral cavity, manually rotate the electrode 28 about axis 56 to the desired orientation and then reposition the tool within the oral cavity against the desired tooth surface. If electrode 28 were not rotatable then the operator would have to change tools, a considerable inconvenience, to treat an opposite tooth surface. The interference fit is designed to permit the electrode to be rotated by gripping it between the forefinger and thumb and yet have sufficient friction so that the electrode will reliably retain the position as set and not rotate upon mere light contact between the end face 58 and a tooth surface or other part of the oral cavity.

FIG. 2 also shows an electrically conductive pathway in the form of wires 64 which are arranged lengthwise along hand piece 22 and connect the prongs 30 to the electrode poles 40 and 44 for powering the electrode 28 by the ESU when the prongs are connected to the ESU power cord. Wires 64 connect to their respective electrode poles by means of contacts 66 and 68 embedded within body 50.

Figure 12:
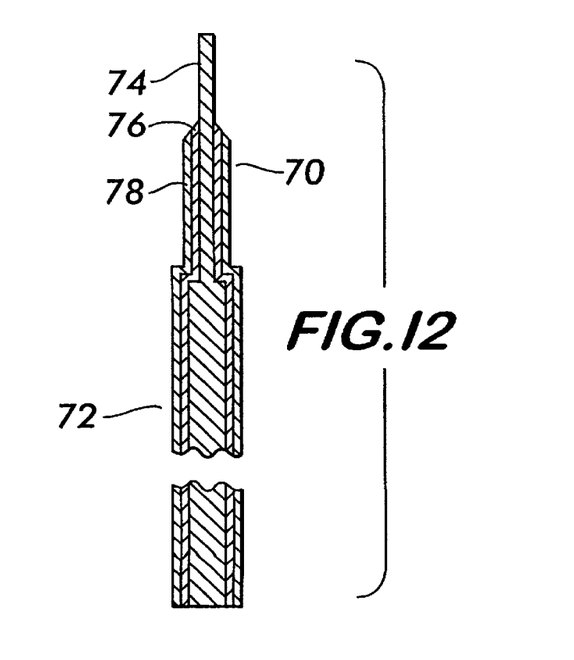
FIG. 12 is a sectional view of a component of the tool.

Preferably, the contacts 66 and 68, as well as the socket 46, are sized to accept a standard electrode end 70 which is the same size regardless of the size of the electrode. FIG. 12 shows an example of a larger size electrode 72 having a standard electrode end 70 for use with the hand piece 22 according to the invention. Standard electrode end 70 has an inner electrode pole terminal 74 which is coaxial with an insulating layer 76 and an outer electrode pole terminal 78. Preferably, inner electrode pole terminal 74 extends lengthwise beyond the outer electrode pole terminal and has a diameter sized to engage contact 66 within body 50 (see FIG. 2). The outer electrode pole terminal 78 has an outer diameter sized to engage contact 68 as well as to interfit within socket 46 (see FIGS. 2 and 4) and provide the interference fit between the electrode 28 and the body 50, creating the necessary friction to retain the electrode within the socket and prevent any undesired rotation. By standardizing the sockets, contacts and electrode ends and making the electrodes easily interchangeable, the versatility of the tool is increased and the duplication of tools merely to use electrodes having different sizes or shapes is eliminated.

Figure 4:
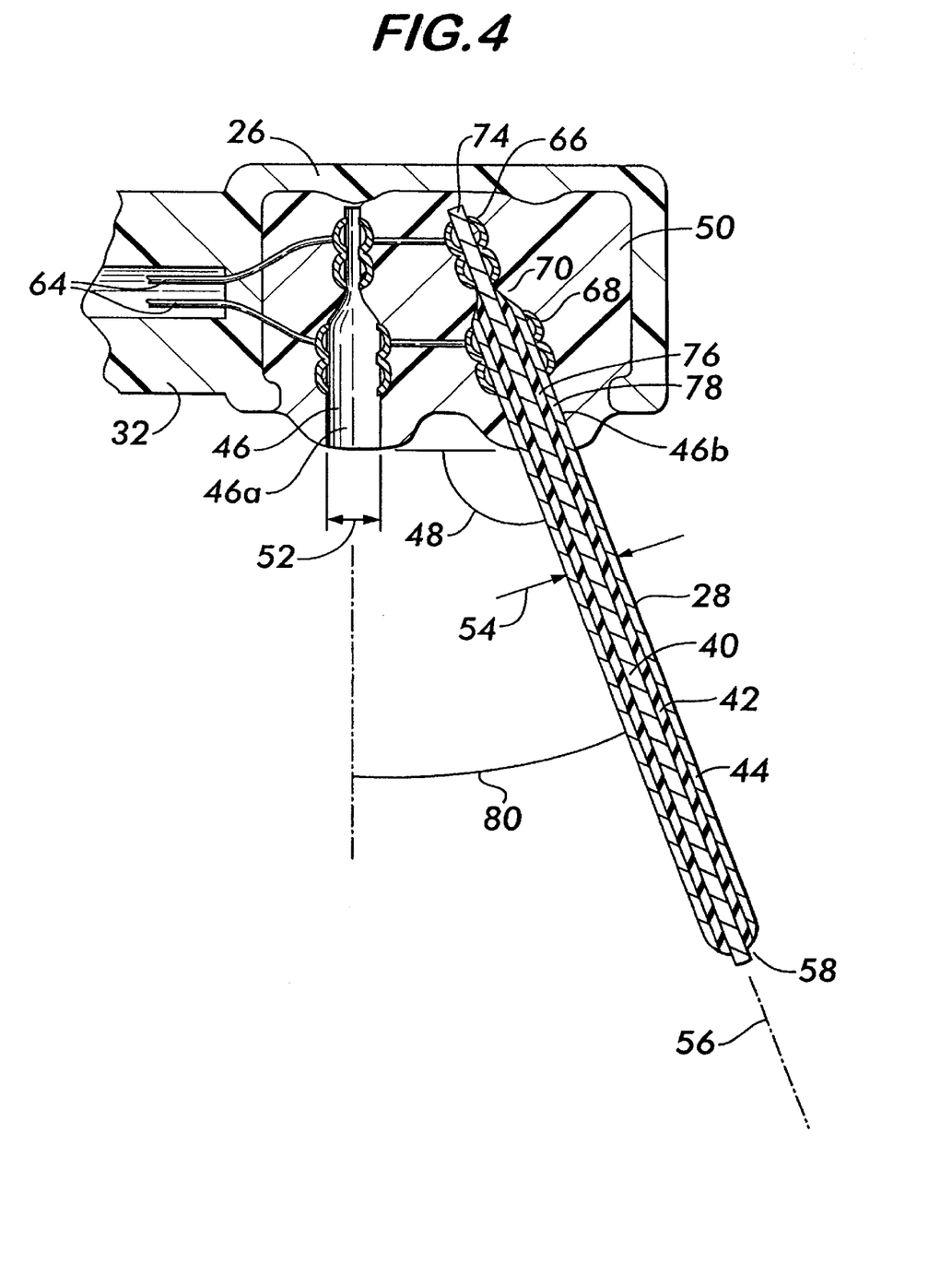
FIG. 4 is a detailed sectional view of a portion of the tool.
Figure 5:
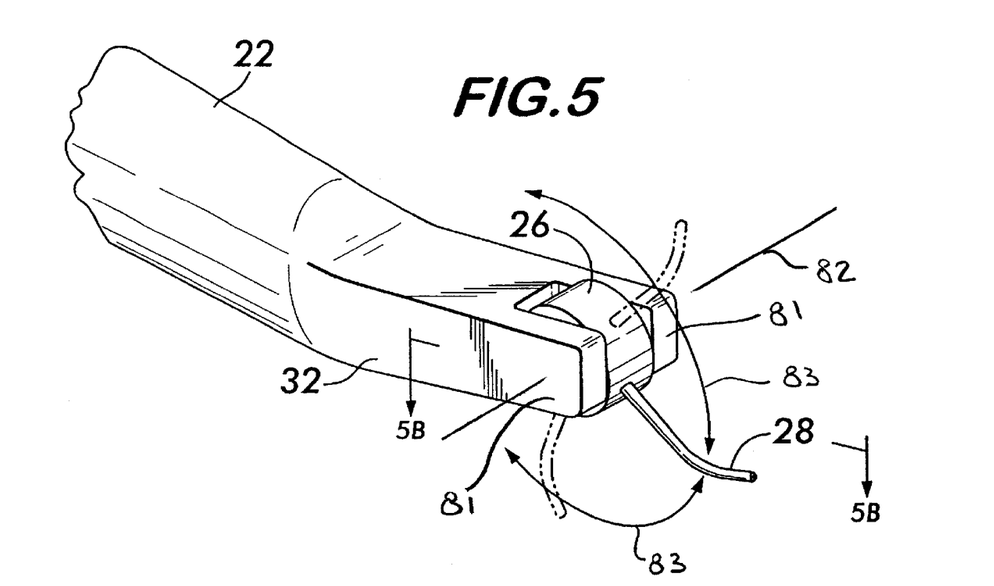
FIG. 5 is a perspective view of a portion of the tool illustrating an alternate embodiment.

Versatility and ease of use of the tool are further increased by the features shown in FIGS. 4 and 5. FIG. 4 shows a head 26 having two sockets 46a and 46b. Socket 46b is oriented at an angle 80 with respect to socket 46a and electrode 28 may be inserted into either one of the sockets as needed to most conveniently treat a particular tooth surface. As described above, the electrode is held within the socket by friction and is rotatable about its long axis 56. Preferably, an insulating plug (not shown) is inserted into the socket not having an electrode to prevent debris from accumulating within it.

Figure 5A:
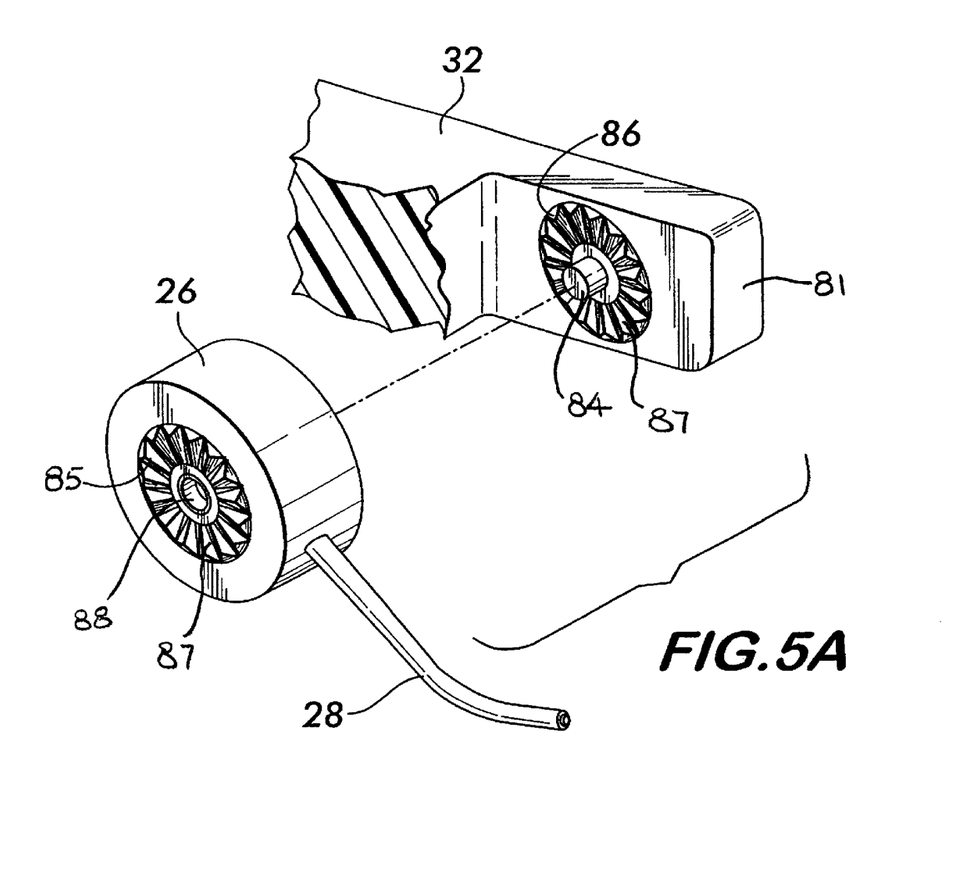
FIG. 5A is a partial exploded perspective view of a portion of the tool shown in FIG. 5.
Figure 5B:
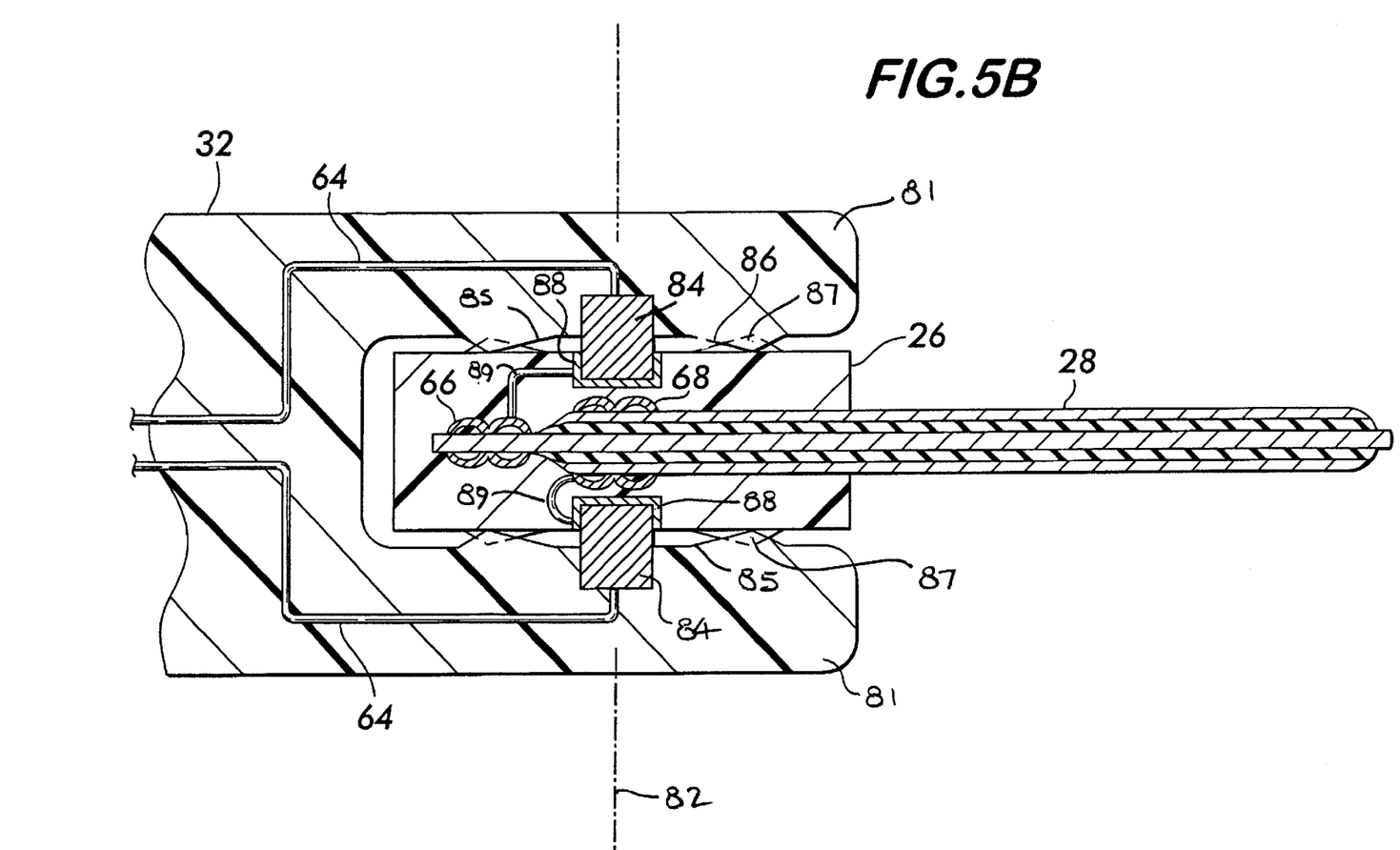
FIG. 5B is a partial sectional view taken along lines 5—5 of FIG. 5.

FIG. 5 shows a head 26 which is pivotally mounted on neck portion 32 between two flanking portions 81 which extend from neck portion 32 on either side of head 26. Head 26 pivots about an axis 82 which is substantially perpendicular to both hand piece 22 and electrode 28. The relative pivot angle 83 of the head 26 may be adjusted manually. As shown in FIGS. 5A and 5B, head 26 is rotatably mounted on inwardly projecting trunnions 84 extending from flanking portions 81 and has outwardly facing side surfaces 85 which engage respective inwardly facing surfaces 86 on flanking portions 81. Surfaces 85 and 86 preferably have interlocking teeth 87 to hold the head 26 securely in a desired angular position by bearing contact between them. Alternately, the surfaces 85 and 86 may be textured, knurled, have detents or other means for locking the head in a desired angular position. Preferably, flanking portions 81 are formed of a flexible, resilient material and are biased toward each other so as to force the surfaces 85 and 86 normally into engagement, thereby locking the head 26 in position. However, upon manual rotation of the head 26 about axis 82, teeth 87 ride over each other, forcing the flanking portions 81 to move outwardly and allow the head 26 to rotate. The flanking portions are flexible and resilient and move back into their biased position to lock the head 26 in place once the desired position is reached and the teeth are again in interlocking, bearing contact.

As best illustrated in FIG. 5B, the trunnions 84 are received within electrically conducting cups 88 arranged within head 26 coaxially with axis 82. The cups 88 serve as bearings for the rotation of head 26 and are electrically connected to respective contacts 66 and 68 by wires 89. Trunnions 84 are also electrically conductive and connected to wires 64. Together, the cups 88 and trunnions 84 provide for an electrical connection between the ESU and the electrode 28 across relatively rotating members 32 and 26.

Various different electrodes, illustrated in FIGS. 2 and 6–12, may be used effectively with the tool 20 according to the invention. Common to all of the electrodes is the standard end 70 engageable with the standard socket 46 regardless of electrode size or shape. Practical sizes for electrodes vary, with the preferred range being between 18 gauge and 23 gauge for treating dental pulp.

The straight electrode illustrated in FIG. 2 preferably has a dome-shaped end face 58, created by extending the inner pole 40 lengthwise beyond the insulating sleeve 42 and the outer pole 44. The preferred lengthwise distance 90 between the inner pole 40 and the outer pole 44 is about 0.05–0.5 mm and determines the depth of penetration of coagulation into the tissue being treated. The greater the distance 90 the deeper the coagulation penetration. This relation between coagulation depth and lengthwise distance 90 is due to the nature of the bipolar coaxial electrode, which causes coagulation only in the zone where current flows between the inner and outer electrode poles 40 and 44. For the dome-shaped end, the current flows in an imaginary conical segment between the poles and the greater the distance between the poles, the greater the height of the conical segment, and hence, the greater the depth of penetration for coagulation. As explained previously, the advantage of the tool according to the invention lies in the relatively shallow coagulation depth, which is achieved by limiting the lengthwise distance 90 between the electrode poles to within the preferred range defined above.

As shown in FIGS. 6 and 7, the electrode 28 may also be curved. Curved electrodes orient the end face 58 asymmetrically with respect to the electrode's long axis 56, and when the electrode is rotatable within socket 46, afford the significant advantage illustrated in FIG. 3 where the same tool may be used to treat opposite surfaces of the teeth. Alternatively to being dome-shaped, the end face may be a cut-back type, as illustrated in FIGS. 8–11.

Figure 10:
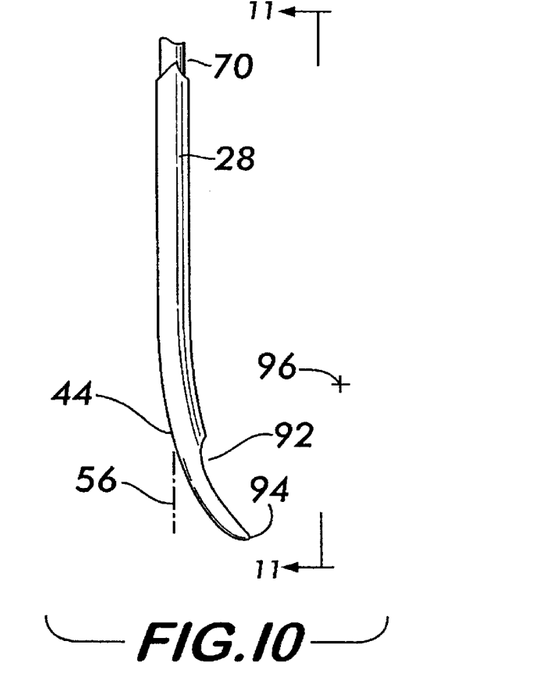
FIG. 10 is a side view of a component of the tool.
Figure 11:
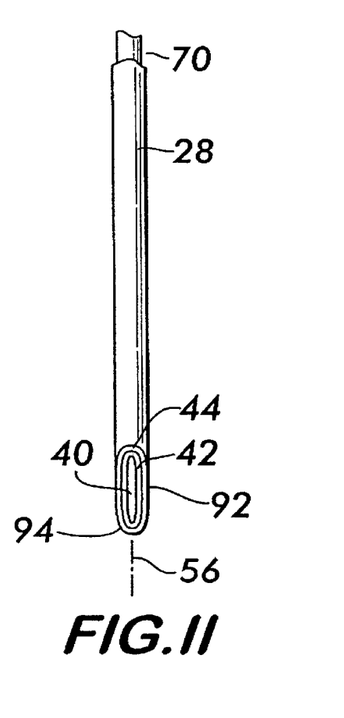
FIG. 11 is a view of the component shown in FIG. 10 taken along lines 11—11.

FIGS. 8 and 9 show an electrode 28 having a cut-back end face 58, wherein the outer electrode pole 44 and the insulating sleeve 42 are cut away asymmetrically on one side of the electrode along a region 92 at the electrode tip 94 to expose the inner electrode pole 40. Preferably, about 40% of the electrode is removed over a length of about 1.0–3.0 mm. Current may flow from the inner electrode pole 40 to the outer pole 44 along the entire length of region 92 and the cut-back results in a larger, elongated zone of coagulation when such a tip is used to treat tooth pulp, gingiva or other soft tissue in the oral cavity. The cut-back electrode may be straight or curved as illustrated in FIGS. 8 and 9. When the electrode is curved, the cut-back region 92 may be positioned on the convex side of the electrode (the side opposite to the center of curvature 96), as shown in FIG. 8, or the cut-back region 92 may alternatively be positioned on the concave side of the electrode as shown in FIG. 10. Regardless of whether the electrode is curved and has a dome-shaped end face 58 or is cut-back, it is the asymmetric orientation of the end face relatively to the electrode's long axis, combined with the ability to rotate the electrode about this axis which significantly improves the versatility of the tool.

When coagulation occurs, the coagulated tissue has a tendency to stick to the end face of the electrode. If not removed, the coagulant layer reduces the effectiveness of the electrode. The choice of alloy and polishing procedures used on the electrode end face can influence the degree of "sticking" of the coagulated tissue. The optimal alloy used in the electrode would be determined based primarily on a determination of which alloy provided the greatest conductivity while resulting in minimal sticking of coagulated tissue. Accordingly, the electrodes used in the present invention are made of any suitable conducting material, preferably from a non-sticking nickel and/or stainless steel alloy.

F. Electrosurgical Unit

The electrodes are preferably used with a bipolar electrosurgical unit (ESU), which includes a timer to control the impulses in fractions of a second. The timer can be regulated by the operator and is pre-set for the specific electrode, ESU and power level to be used. Some units include timers for specific therapeutic objectives (e.g., coagulation for reduction of the size of the uvula (8 sec range)).

Many bipolar electrosurgical units are available with a variety of current frequencies and current types (e.g., various waveform types, damping, work cycle).

The general requirements for a bipolar ESU are as follows:
Power Output: 0–20 watts as measured against 100 Ohm resistance
Power Supply: 115 V, 60 Hz (optional 220 V, 50 Hz)
Frequency: Optimum 500 KHZ (other frequencies will also work)
Current: Optimum—smooth, non-modulated, continuous RF-current (other currents will also work with appropriate calibration with electrodes.)
Cable: Teflon coated twin-wire 6–10 foot cable
The ESU preferably has power output in the range of about 0.0 to about 20.0 watts. A number of criteria define what frequencies should be used with the unit. Firstly, a frequency must be sufficiently high to prevent stimulation of muscles and nerves. Available electrosurgical frequencies are well above these levels. Secondly, heat is generated by the rapid oscillation of charged molecules caused by the alternating polarity of the alternating electrosurgical current. This is referred to as the dielectric effect and increases with an increase in the frequency of the alternative current. What portion of the heat generated is due to the dielectric effect and what portion is due to resistance (impedance) of the tissue is unclear. Frequencies in the range of 0.5 to 4.0 MHZ are typically used in electrosurgery with the most often used frequencies occurring in the 0.5 to 2.0 MHZ. Thirdly, the higher frequencies (3.0 to 4.0 MHZ) result in more current loss due to the radiating properties of electrosurgical currents. This factor encourages the use of lower frequencies.

Low power microsurgical units range from 0–15 watts, while high power units used for prostate resection can provide 300 or more watts. Based on the type of tissue, the volume of tissue and the precise nature of coagulation desired in pulpal hemostasis, an electrosurgical unit providing power output in the range of 0–20 watts (measured against 100 Ohm resistance) is preferred.

The ESU of the present invention preferably includes an electronic timer which can be set for the appropriate time intervals for each electrode (0.05 to 0.5 sec) to create the optimal level of coagulation. The optimal level of coagulation is determined by establishing durable hemostasis with minimal surgical wound. Durable hemostasis can be ascertained clinically using (1) vital pulps; (2) an intact circulation; (3) actual pulp tissue; and (4) conditions and circumstances that will be confronted in actual pulp therapy. Minimal surgical wound can be observed and established with each electrode design by utilizing the electrode on tissue specimens such as beef steak, beef liver, animal intestinal walls or animal blood vessels. An example of how to determine the optimal level of coagulation is presented in Example 2 hereinbelow.

The implementation of the timer enables another level of safety and precision when attempting to coagulate extremely small areas and for extremely shallow depths. The combination of a ESU, a coaxial electrode, and a timer allowing intervals in fractions of a second enables the ultimate precision in coagulation. Once the tissue at the end of the electrode coagulates, the increased resistance (impedance) of the tissue prevents flow of current. This self-limiting capability of the coaxial electrode replaces more complex systems, e.g., impedance monitoring of the active electrode or temperature monitoring of the tissue at the active electrode.

In order to establish the optimum power/time settings ("hemostatic combination"), the type of electrode, the size of each pole of the electrode, the type of metal composing the electrode and numerous other aspects must be considered to optimize treatment.

The optimal configuration for the electrode is established by the location and size of the most typical exposures expected to be confronted. Since most exposures occur because of decay on the mesial and distal sides of teeth (between teeth), an electrode would require a right-angle bend with a 10 mm extension beyond the bend. Preferably, an about 18 gauge electrode is used to treat lesions due to decay while an about 23 gauge electrode is preferably used for coagulation within the root portions in overdenture applications.

The optimal power/time combination will provide uniform coagulation throughout the footprint of the electrode. An example of how to determine the optimal power/time combination is presented in Example 3.

The coaxial design provides the most consistent, shallow and optimal form of coagulation with the greatest safety and minimal surgical wound. By relying on bipolar coagulation and a specific coaxial electrode, the volume of tissue to be coagulated is consistent, and by relying on the bipolar mode and using a coaxial electrode configuration, the path of the current is consistent. The frequency and current type of the ESU is established by the manufacturer which are initially factored in the calibration of the "hemostatic combination" and, therefore, consistent. The use of a pre-determined optimal time which has been found to be in fractions of a second (e.g., 0.5 sec impulse) provides another level of consistency. Given the difficulty in manually controlling the output of the ESU in fractions of a second, the timer is an important component in providing consistency and a greater level of safety to the pulp.

G. Pulp Barrier

The methods related to the present invention include use of components for replacing the lost pulpal wall. These components are included to provide retention for the pulp barrier independent of the external restoration. The long term integrity of the pulp barrier: (1) should not be linked to the stresses applied to the external restoration; (2) should not be determined by the success/failure of the external restoration; and (3) the pulp barrier should not provide the principal support or retention for the external restoration. The external restoration should rely on traditional cavity preparation components for retention and resistance to prevent displacement outward. This protocol, however, emphasizes the incorporation of retentive components to also prevent inward displacement of the external restoration. Contrary to recommendations by many lecturers and manufacturers of adhesive restorative materials, the adhesion that occurs between a resinous pulp barrier and an adhering external restoration should be directed to preventing microleakage and not relied upon for the basic retention of the restoration. If and when an external restoration fails or needs replacement, ideally the pulp barrier should remain intact. Traditional cavity preparation components for retention include undercuts, grooves or threaded pins.

The material used for replacing the lost portion of the pulpal wall preferably comprises an adhesive resin barrier material which creates an effective hybrid layer and is biocompatible with the pulp. A variety of resinous materials may also prove useful as a long-term pulp barrier.

A wide range of resins have been introduced in dentistry to achieve adhesion between the dentin and the external restoration with the objective of reducing microleakage and the ingress of bacteria from the oral cavity to the internal walls of the cavity preparation. With a substantial dentinal wall remaining over the pulp, the biocompatibility of the resins with the pulp is not an important concern. However, when such resins are applied in direct contact with pulpal tissue, the biocompatibility issue is crucial.

The methods associated with the present invention go beyond current procedures to utilize resins as the restorative material to reconstruct the missing pulpal wall. Hence, the resin is referred to as a "pulp barrier" rather than a "pulp capping" material. Traditional pulp capping materials served to provide medicaments to the pulp, to provide thermal protection (insulation) and to stimulate reparative dentin via a mild irritating effect on the pulp.

A preferred resin material is a 4-META adhesive resin system (Metabond C&B; Parkell Dental Products, Farmingdale, N.Y.) which can be used to replace the missing segment of the pulpal wall and which has demonstrated the ability to create an effective seal (hybrid layer). The 4-META resin may be applied according to the instructions of the manufacturer. Studies support a degree of biocompatibility with pulpal tissue.

Preferably, the resin used to restore the pulpal wall includes a visible dye such that the resin is color coded, serving to warn dentists performing subsequent procedures not to violate the pulpal wall barrier. A variety of dyes are known in the dental arts, and any dye that is non-toxic and which retains its color are preferably used in the practice of the invention.

EXAMPLES

Example 1

Pulp Hemostasis Method

The following example describes the use of the methods and apparatus of the present invention for pulp hemostasis.

The tooth is examined clinically and radiographically. Clinical symptoms are recorded for comparison with subsequent evaluations. Evidence of periapical inflammation is also noted (tenderness to percussion of the tooth and apical radiolucency). Vitality of the tooth is determined by sensitivity to ice, electric pulp testing or sensitivity to instrumentation such as cavity preparation prior to local anesthetic. If the pulp is diagnosed as necrotic, the tooth is planned for extraction or endodontic therapy since pulp therapy is not possible.

Once vitality is established the tooth is anesthetized with local anesthetic. If the carious lesion does not extend subgingivally, a rubber dam may be placed for improved isolation.

The outline form for the planned cavity preparation is completed according to traditional guidelines avoiding temporarily the removal of deep caries. Deep caries excavation with the probable exposure of the pulp is postponed until the majority of the cavity preparation is completed to minimize debris from entering the pulpal space.

Once the cavity preparation is completed, deep caries is removed with a large sharp spoon excavator or a round bur on a low speed handpiece.

Caries excavation is completed despite initial exposure of the pulp. Thorough excavation of caries should be accomplished. Unlike past "pulp capping" procedures in which the prognosis was considered better if the exposure was kept small, in vital pulp therapy described in this protocol the prognosis is improved by removal of all affected and compromised dentin. [Affected and compromised refers to the (1) decalcification of the remaining dentin, (2) inclusion of bacteria or bacterial by-products, and (3) potential collapse of thin areas of dentin.] Vital pulp therapy encourages more thorough removal of caries and affected dentin.

Bleeding of the pulp during caries excavation and cavity preparation should be encouraged since the flushing action of the bleeding will reduce the debris that may become incorporated in the pulp.

Once the cavity preparation is completed, vitality of the pulp is confirmed by the presence of both blood (intact circulation) and pulp tissue. Blood alone can sometimes occur from the apical region or from another canal despite a necrotic pulp in one or more canals. Instrumentation and materials are then prepared for hemostasis and formation of the pulp barrier (restoration of the pulpal wall).

A Kirwan 18 g coaxial bipolar electrode used in ophthalmology is used to provide hemostasis in pulp therapy utilizing an Elmed Micro Electrosurgery Unit with power output (against 100 Ohm resistance) of about 0 to about 20 watts and a frequency of 500 MHZ. the unit is combined with an electronic timer providing 0.5 sec interval of power with each press of the foot switch. The power setting of the unit is set to #6 providing 5 watts of power at the unit (determining the actual power at the tissue surface is difficult and may vary for many reasons; e.g., length of cable, deterioration of cable, radiating potential of high frequency causing current loss, etc.). The electrode is attached to the unit via a 6 foot Teflon covered cable.

The coaxial electrode is placed in contact with the pulp tissue and the foot control is engaged to provide one impulse of 0.5 sec duration. If the exposure is larger than the end of the electrode and bleeding is occurring from other points, the electrode is moved and another 0.5 sec impulse is applied. This sequence is continued until the entire surface of the pulp is coagulated. The size of the exposure is inconsequential. If one of the impulses did not achieve hemostasis, another impulse can be applied over the same area. By using the coaxial electrode, the depth of coagulation is not cumulative but more "compensatory", i.e., tissue already coagulated develops a higher resistance (impedance) and inhibits further coagulation while adjacent unaffected tissue will be susceptible to coagulation. The coaxial electrode has the capability to control the flow of current to the area immediately under the electrode tip. Indeed the same area can receive numerous coaxial impulses with virtually no increase in depth of coagulation. Rarely will it be necessary to increase the power, and when that option is selected, it is increased only one setting (approximately 1–2 watts).

Once hemostasis is achieved, it is checked for durability by swabbing the pulpal surface with a cotton pellet moistened with water or saline. If bleeding recurs, coagulation is repeated. Specific bleeding points will be more visible and readily coagulated since most vessels have been sealed previously. The durability check is important since it is crucial that bleeding does not recur while the barrier is being formed.

Once durable hemostasis is accomplished, an adhesive resin barrier material which creates an effective hybrid layer and is biocompatible with the pulp is applied according to the instructions of the manufacturer. (4-META adhesive resin system (Metabond C&B; Parkell Dental Products, Farmingdale, N.Y.). The material is applied in increments with a brush tip to minimize the polymerization shrinkage. Additional retentive components may be incorporated after complete setting of the barrier material. The remaining dentin and enamel are prepared for a sealed external restoration.

The external restoration is then placed according to traditional procedures.

The patient is recalled 3, 6 and 12 months for recall evaluation using the same criteria as the pre-treatment examination.

Example 2

Determination of Optimal Coagulation

A new coaxial electrode with a given outer diameter will be coupled with a Elmed Microsurgical Unit and a six-foot cable. The optimal and consistent coagulation ("hemostatic combination") for that electrode will be defined by (1) uniform coagulation throughout the electrode "footprint" (surface area of the end of the electrode tip), and (2) minimal depth of coagulation (0.25 to 0.5 mm depth). By varying the power output to the electrode one will observe, with insufficient current, that a "donut" configuration of coagulation occurs with an inner zone of uncoagulated tissue and an outer rim of coagulation following the outline of the outer tube of the electrode. As the power output is increased, the zone of coagulation becomes uniform throughout the entire surface (footprint) of the electrode tip. Further increasing the power output is redundant with the coaxial electrode. The coaxial electrode is self-limiting in coagulation which is one of the highly-valued properties and safety features for applications in pulp therapy. Increasing the power output with other types of electrodes increases the "area" of coagulation, the "depth" of coagulation and the "degree" of coagulation proceeding from the lower acceptable levels of white coagulation, through the optimal level of desiccation, to the higher unacceptable levels of black coagulation (charring).

Thus, by varying the power levels and impulse time intervals, an optimal "combination" can be established for each electrode design and size.

Example 3

Determination of Optimal Power and Time Settings for ESU

To establish the optimal power/time combination, the electrode would be used on liver tissue beginning with a fixed time interval selected within a reasonable range of 0.01 to 1.0 seconds. While intervals in the range of several seconds at very low power would also create coagulation, substantial lateral heat and a broader area of coagulation would occur which is not desirable. Beginning with the lowest power setting on the electrosurgical unit, areas would be coagulated on the liver until the optimal coagulation zone is achieved (uniform coagulation throughout the "footprint" of the electrode). The power would be increased further to ascertain that the lower power levels provided the optimal coagulation.

Figure 13:
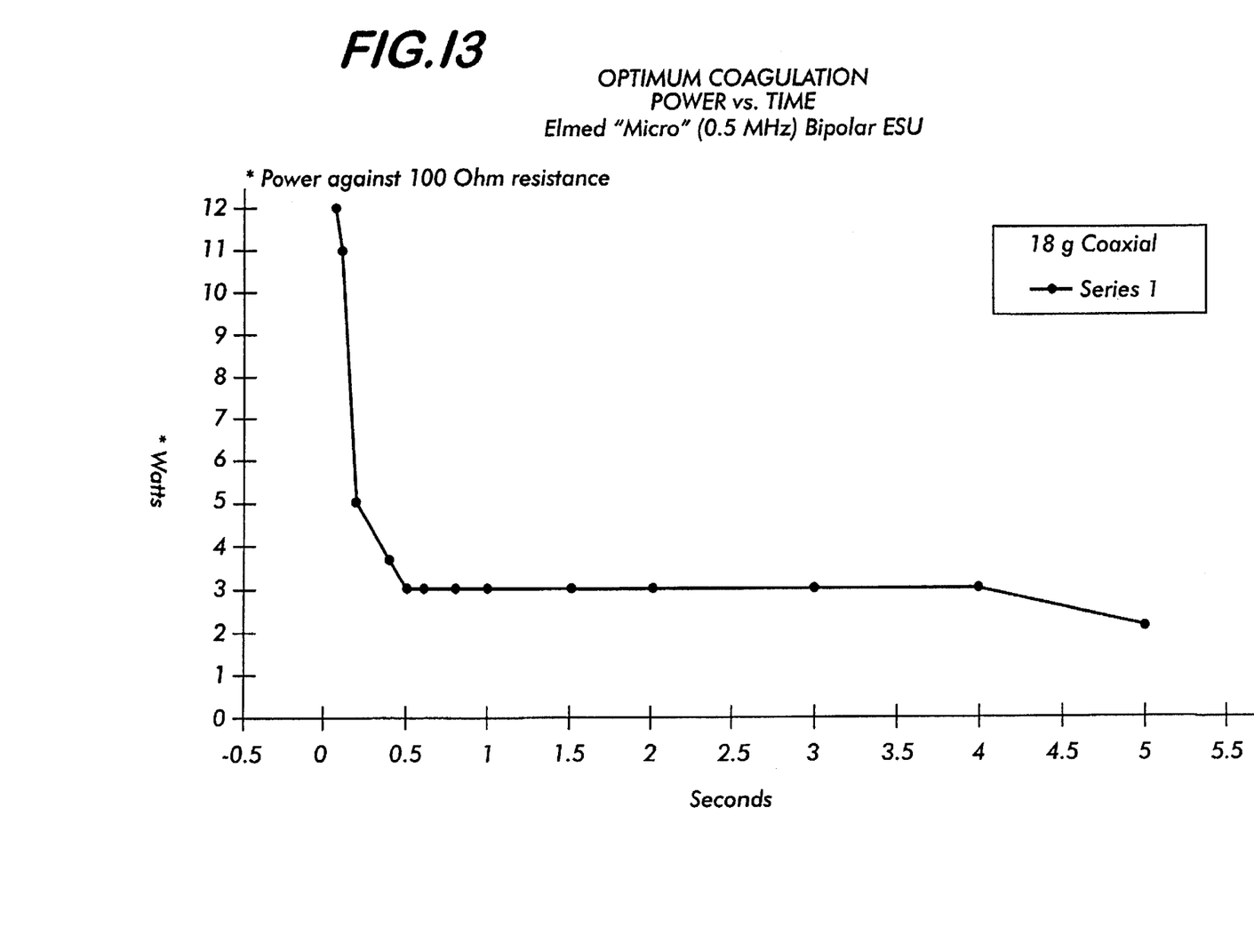
FIG. 13 is a graph used to determine the optimal time and power settings for coagulation.

One of the lowest power output levels that achieved optimal coagulation would then be selected (several levels may be available) as the fixed power output level. The same process would be repeated by varying the time interval to establish the minimum time intervals that provide the optimal zone of coagulation. Once both series are plotted, the minimal time is coupled with the minimal power to establish the optimal combination for that electrode design. Although several combinations may be found suitable, they will all fall within a narrow range. An optimal time/power "hemostatic combination" can readily be established in the mid-range providing some latitude for the operator. Such a graph is provided in FIG. 13 to illustrate how definitively the optimum combination can be established.

What is claimed is:

1. An electrosurgical tool for use with an electrosurgical power unit for coagulating a tissue layer, said tool comprising:
    an elongated hand piece having a butt end and a head oppositely disposed, and a longitudinal axis;
    an electrical coupling mounted on said butt end and adapted to connect electrically to said electrosurgical power unit;
    an electrically conductive pathway arranged lengthwise along said hand piece and connected to said electrical coupling; and
    an elongated electrode mounted on said head and connected to said electrically conductive pathway, said electrode having a long axis oriented at an angle relatively to said longitudinal axis of said hand piece, said electrode being rotatable about its long axis.

2. A tool according to claim 1, wherein said electrode is a bipolar electrode having first and second electrode poles.

3. A tool according to claim 2, wherein said electrode is a coaxial electrode having said first electrode pole coaxially surrounded by said second electrode pole, an insulating layer being coaxially positioned between said first and said second poles.

4. A tool according to claim 3, wherein said electrode has an end face positioned distally to said head, said end face being formed by extending said first electrode pole lengthwise beyond said second electrode pole, said end face being oriented at an angle relatively to said long axis.

5. A tool according to claim 4, wherein said end face is oriented at an angle between about 15° to about 45° to said long axis.

6. A tool according to claim 4, wherein said electrode is curved, thereby orienting said end face at said angle to said long axis.

7. A tool according to claim 3, wherein said electrode has an end face positioned distally to said head, said end face comprising a cut-back region formed by removing a lengthwise portion of said second pole and said insulating layer along one side of said electrode to expose said first pole along a portion of said one side.

8. A tool according to claim 7, wherein said electrode is curved about a center of curvature, said electrode having a convex side facing away from said center of curvature and a concave side facing toward said center of curvature.

9. A tool according to claim 8, wherein said cut-back region is positioned on said convex side of said electrode.

10. A tool according to claim 8, wherein said cut-back region is positioned on said concave side of said electrode.

11. A tool according to claim 1, wherein said electrode is oriented substantially at a right angle relatively to said hand piece.

12. A tool according to claim 1, wherein said hand piece comprises a neck portion positioned adjacent to said head, and a grip portion positioned between said neck portion and said butt end, said neck portion being oriented at an angle relatively to said grip portion.

13. A tool according to claim 12, wherein said neck portion is oriented at an angle between about 20° and about 30°.

14. A tool according to claim 12, wherein said neck portion is oriented at an angle of about 25°.

15. A tool according to claim 1, wherein said head is pivotally mounted on said hand piece for pivoting motion about an axis substantially perpendicular to both said hand piece and said electrode.

16. A tool according to claim 1, wherein said head further comprises a socket sized to receive said electrode for mounting said electrode on said head, said socket having electrical contacts positioned therein connecting said electrode to said electrically conductive pathway.

17. A tool according to claim 16, wherein said head further comprises a plurality of said sockets.

18. A tool according to claim 17 wherein said sockets are oriented angularly with respect to one another, said electrode being engageable with any one of said sockets to orient said electrode angularly with respect to said head.

19. An electrosurgical tool for use with an electrosurgical power unit for coagulating a tissue layer, said tool comprising:
    an elongated hand piece having an electrical coupling positioned at one end and a socket at the other end, said electrical coupling being adapted to connect electrically to said electrosurgical power unit, said socket having a pair of electrical contacts therein;
    an electrically conductive pathway extending lengthwise along said hand pieced connecting said contacts to said electrical coupling; and
    an elongated coaxial bipolar electrode sized to interfit within said socket and engage said contacts, said electrode being oriented at an angle to said hand piece and comprising a first electrode pole coaxially surrounded by a second electrode pole, an insulating layer being coaxially positioned between said first and said second poles, said electrode being rotatable about its long axis within said socket and having an end face positioned distally to said socket and arranged asymmetrically with respect to said long axis.

20. A tool according to claim 19, wherein said socket is located within a body of resilient, flexible insulating material attached to said other end of said hand piece, said socket being sized smaller than said electrode to provide an interference fit therebetween so as to removably retain said electrode within said socket and allow said electrode to rotate about said long axis.

21. A tool according to claim 19, further comprising a plurality of said sockets positioned at said other end, said sockets being angularly oriented relatively to one another for orienting said electrode angularly with respect to said hand piece when received within one of said sockets.

22. A tool according to claim 19, wherein said end face is formed by extending said first electrode pole lengthwise beyond said second electrode pole.

23. A tool according to claim 22, wherein said electrode is curved, thereby orienting said end face asymmetrically with respect to said long axis.

24. A tool according to claim 19, wherein said end face comprises a cut-back region formed by removing a lengthwise portion of said second pole and said insulating layer along one side of said electrode to expose said first pole along a portion of said one side.

25. A tool according to claim 19, wherein said electrode has a diameter between about 18 and about 23 gage.

* * * * *